(12) United States Patent
Citron et al.

(10) Patent No.: US 6,641,588 B2
(45) Date of Patent: Nov. 4, 2003

(54) SURGICAL TOOL FOR TENSIONING A CRANIAL-FLAP CLAMP

(75) Inventors: Robert B. Citron, Ventura, CA (US); Lawrence L. Hampton, Santa Maria, CA (US); Oliver Buchert, Oakland, NJ (US); Heather Savage, Ventura, CA (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/851,360

(22) Filed: May 8, 2001

(65) Prior Publication Data

US 2002/0169463 A1 Nov. 14, 2002

(51) Int. Cl.[7] .............................................. A61B 17/04
(52) U.S. Cl. ....................................... 606/103; 600/148
(58) Field of Search .................... 606/148, 103, 606/74; 140/123.5, 93.4, 93.2, 93 D; 81/9.4, 9.41, 9.42; 254/237

(56) References Cited

U.S. PATENT DOCUMENTS

| | | | |
|---|---|---|---|
| 1,304,620 A | * 5/1919 | Steinkoenig | |
| 2,217,077 A | * 10/1940 | Phillips | 81/9.41 |
| 3,169,560 A | * 2/1965 | Caveney et al. | 140/93.2 |
| 4,321,952 A | * 3/1982 | Natkins | 140/93.2 |
| 4,733,701 A | * 3/1988 | Loisel et al. | 140/93.2 |
| 5,048,575 A | * 9/1991 | Smith | 140/93.2 |
| 5,388,619 A | * 2/1995 | Ghawi | 140/93.2 |
| 5,632,312 A | * 5/1997 | Hoffman | 140/93.2 |
| 6,022,351 A | 2/2000 | Bremer et al. | |

FOREIGN PATENT DOCUMENTS

| | | |
|---|---|---|
| DE | 19634699 | 4/1998 |
| DE | 29812989 | 11/1998 |
| DE | 19952359 | 3/2001 |
| EP | 0920837 | 6/1999 |

OTHER PUBLICATIONS

Article entitled: "Bone Flap Fixation With Titanium Clamps: A New Technique", published in Elsevier Science Inc. 2000.

Article entitled: "Reliability of Cranial Flap Fixation Techniques: Comparative Experimental Evaluation of Surturing, Titanium Miniplates, and a New Rivet–like Titanium Clamp (CranioFix): Technical Note", by Karl–Dieter Lerch, published in Neurosurgery, vol. 44, No. 4 Apr. 1999.

Article entitled: "RapidFlap—A Unique Cranial–Flap Closure System For Enhanced Strength, Speed and Savings" published in W.Lorenz Surgical.

* cited by examiner

*Primary Examiner*—Todd E. Manahan
(74) *Attorney, Agent, or Firm*—Kelly Bauersfeld Lowry & Kelley, LLP

(57) ABSTRACT

A surgical tool for tensioning cranial-flap clamps is provided. The tool includes first and second handles pivotally attached to one another. A first jaw extends from the first handle and has an aperture configured to accept a stem of the clamp therethrough. A second jaw extends from the second handle and has an aperture configured to accept a stem of the clamp therethrough. A ratcheting mechanism is positioned within a cavity of the second jaw for selectively locking the stem in place within the second jaw aperture while the first jaw moves clamp closure members toward one another. The ratcheting mechanism includes a pawl pivotally attached to the jaw, and having teeth on an outer edge thereof, and a spring associated with the jaw and pawl to bias the pawl in a locking position when the first and second jaws are separated.

10 Claims, 6 Drawing Sheets

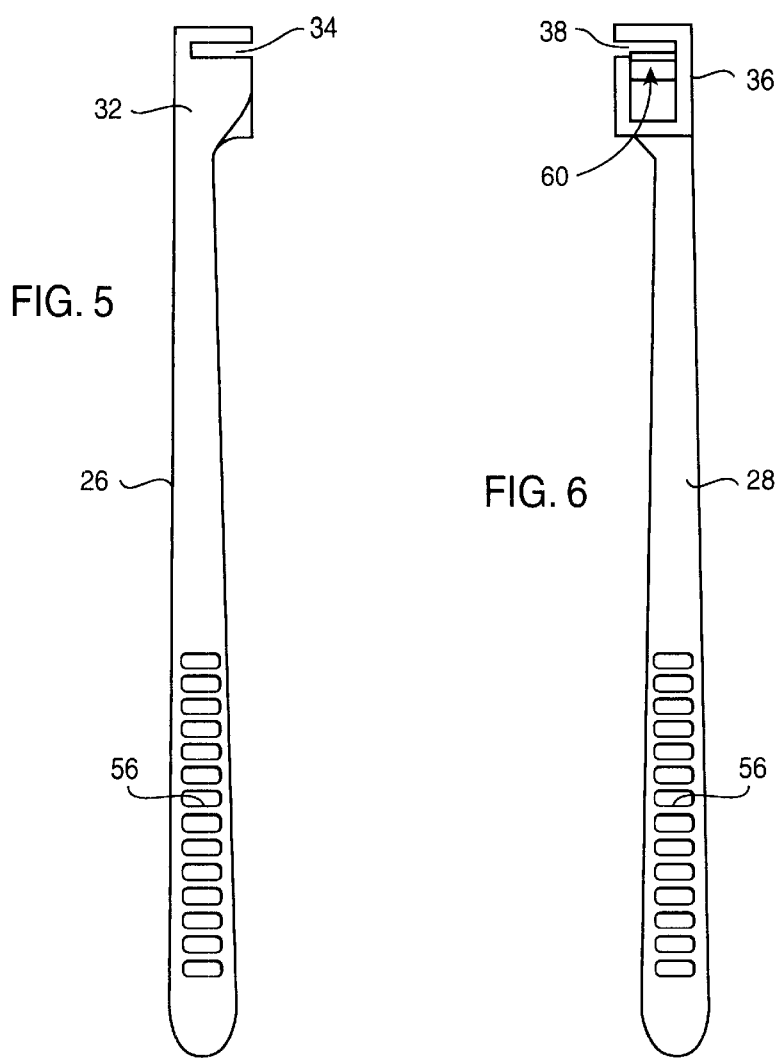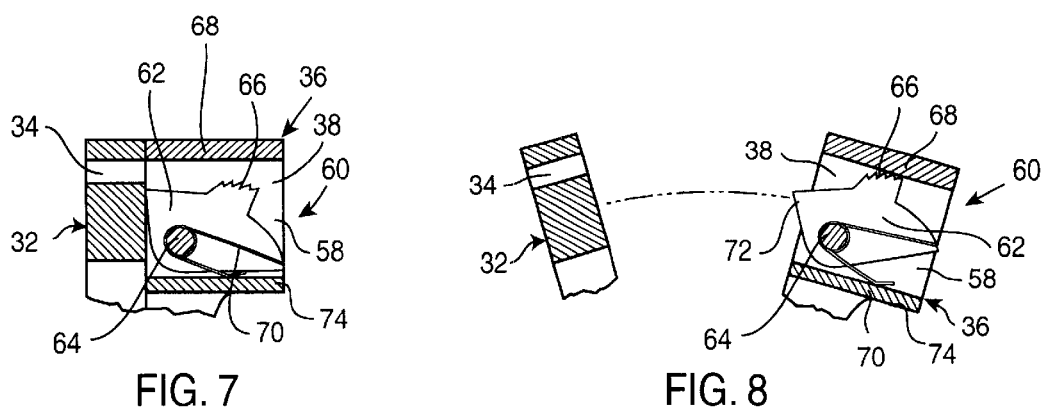

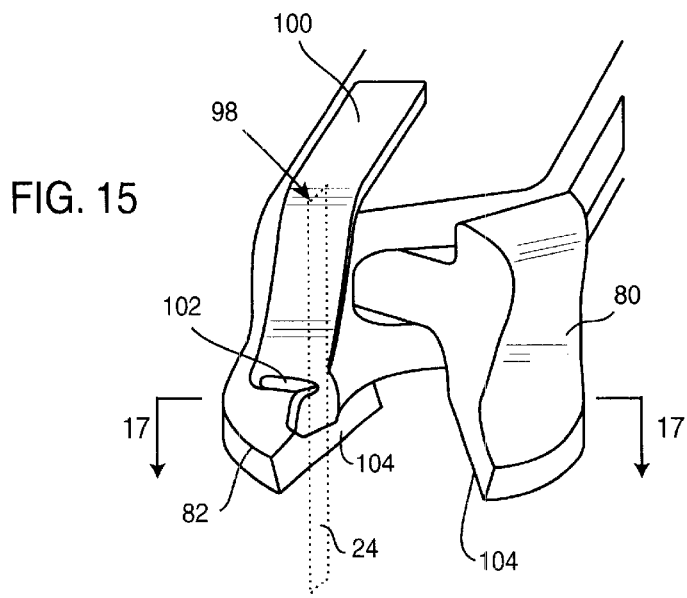
FIG. 15
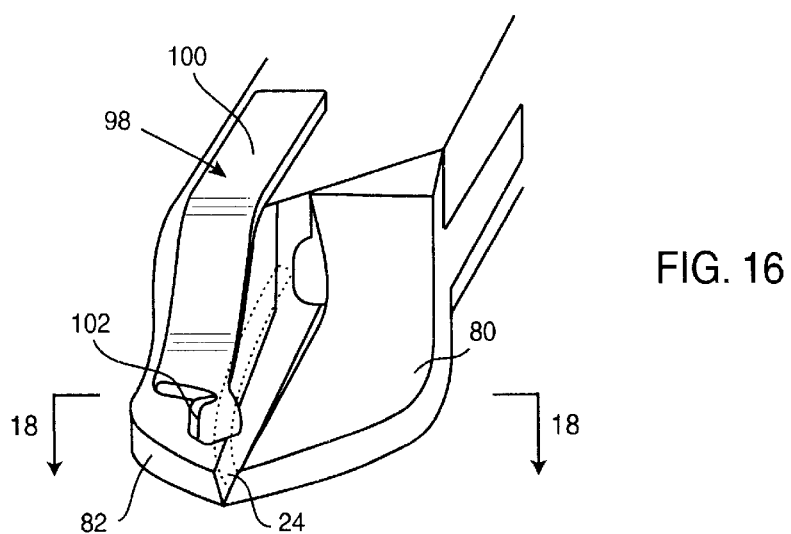
FIG. 16
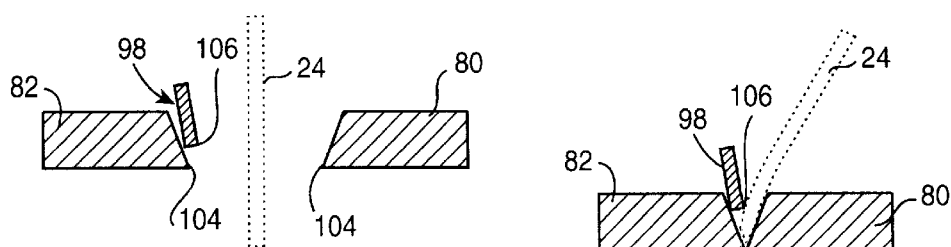
FIG. 17
FIG. 18

SURGICAL TOOL FOR TENSIONING A CRANIAL-FLAP CLAMP

BACKGROUND OF THE INVENTION

The present invention generally relates to skull flap fastening systems. More particularly, the present invention relates to a surgical tool which facilitates the tensioning of a cranial-flap clamp used in such fastening systems.

When brain surgery is performed, it is often necessary to remove a piece of the skull to provide access to the brain. This surgical procedure is often referred to as a craniotomy. A portion of the cranial vault is removed or folded back in a flap to permit surgical access to the cranial contents, such as the brain. This is often done with a hand-held, gas-powered surgical tool similar to a small router. After a small hole is made in which the bit of the router is placed, the bit is then guided to cut out the piece of the skull required. The blade cuts a small gap so that the piece removed does not fit back into its hole exactly.

After the brain operation, the skull flap must be replaced and held in position until the skull heals. Previously, a series of matching small holes were drilled in the edge of the skull and the edge of the skull flap. Sutures were then passed through the corresponding holes and the flap secured back into the skull opening from which it was taken. However, due to the inexact fit caused by the router bit, the flap sat slightly below the surface of the skull, resulting in a depressed area visible through the skin.

Stainless steel wire was substituted for the suture material, which is stronger than the suture material, but more cumbersome. The wire was prone to failure, particularly if over-twisted, and was found to be palpated through a skin scalp if not properly buried. Also, the introduction of computed tomography (CT), demonstrated extensive metal artifacts caused by these wires. Further, the common problem of skull flap settling remained.

More recently, cranial mini-plate fixation systems were developed. While these systems have been successful, they are time consuming and very expensive.

Even more recently, alternative cranial fixation systems comprised of cranial-flap clamps having opposing closure members, often disks, in which one disk is fixed to an end of a stem, while the other is movable along the stem towards the opposing closure member to clamp the skull and bone flap together. This method is faster than any of the other methods and less expensive and time consuming than the mini-plate fixation systems.

Tools have been devised for gripping the pin or stem of the clamp, and then pressing together the disks into a clamping formation. However, the process often takes more than one tool to complete, thus requiring both hands of the surgeon. Some of the tools require calibration before use. Another disadvantage of such tools is that they require special cleaning processes due to their complicated design. Some surgeons have also found these tools somewhat complicated in use and not intuitive.

Accordingly, there is a need for a surgical tool which is intuitive and easy to use. During tensioning of the clamp, the tool should not require calibration. The tool should also be able to perform the clamping procedure alone, so that a hand of the surgeon is free from the procedure. The tool should not require special cleaning processes, nor disassembly before its next use. The present invention fulfills these needs and provides other related advantages.

SUMMARY OF THE INVENTION

The present invention resides in a surgical tool for tensioning a cranial-flap clamp having opposing closure members variably positioned relative to each other on a stem for refixing a bone flap to the cranium. The tool generally comprises first and second handles which are pivotally attached to one another intermediate their first and second ends. A first jaw extends from the first end of a first handle, and has an aperture which is configured to accept the stem therethrough. A second jaw extends from the first end of the second handle, and has an aperture configured to accept the stem therethrough. A ratcheting mechanism is associated with the second jaw which selectively locks the stem in place within the second jaw aperture. Typically, the first and second jaw apertures comprise open-faced channels extending the width of the first and second jaws.

The ratcheting mechanism preferably comprises a pawl pivotally attached to the second jaw and having teeth on an outer edge thereof. A spring is associated with the jaw and the pawl to bias the pawl in a locking position. The ratcheting mechanism is typically positioned within a cavity of the second jaw which is at least partially contiguous with the second jaw aperture. A portion of the pawl extends without the second jaw when the pawl is in its biased position. The first jaw is configured to contact the pawl and position the pawl in an unlocked position when the jaws are brought towards one another.

The tool includes means for biasing the first and second jaws into contact with one another, such as a spring positioned between the first and second handles. Typically, the spring comprises first and second leaf springs. A first end of the first leaf spring is attached to the second end of the first handle. A first end of the second leaf spring is attached to the second end of the second handle. The second ends of the first and second leaf springs are connected to each other so as to bias the jaws into contact with one another.

In use, the cranial-flap clamp is properly positioned between the cranium and the bone flap. The stem is inserted through the aperture of the first and second jaws. As the tool is actuated by squeezing the second end of the handles, the pawl of the ratcheting mechanism locks the stem in place within the second jaw aperture, while the first jaw presses against the sliding closure member so as to bring the closure members towards one another in a clamping formation. Once proper tension is achieved, the stem is trimmed from the clamp.

The surgical tool of the present invention is advantageous over prior existing tools in that it is easy and convenient to use. Moreover, the tool does not need to be calibrated before use, and does not require disassembly nor special cleaning procedures after use.

Other features and advantages of the present invention will become apparent from the following more detailed description, taken in conjunction with the accompanying drawings which illustrate, by way of example, the principles of the invention.

BRIEF DESCRIPTION OF THE DRAWINGS

FIG. 5 is a side elevational view taken generally along 5—5 of FIG. 3;

FIG. 6 is a side elevational view taken generally along line 6—6 of FIG. 3;

FIG. 7 is a cross-sectional view taken generally along line 7—7 of FIG. 3, and illustrating a ratcheting mechanism;

FIG. 8 is a cross-sectional view taken generally along line 8—8 of FIG. 4;

FIG. 15 is a fragmented perspective view of jaws of the trimming tool of the present invention being placed around a stem in phantom of a cranial-flap clamp;

FIG. 16 is a fragmented perspective view of the trimming tool jaws of FIG. 15 closed upon the stem to cut the stem and retain the stem in the jaws of the trimming tool;

FIG. 17 is a cross-sectional view taken generally along line 17—17 of FIG. 16; and FIG. 18 is a cross-sectional view taken generally along line 18—18 of FIG. 16, illustrating the retention of the stem within the jaws by virtue of a flexible clip associated with the jaws.

DETAILED DESCRIPTION OF THE PREFERRED EMBODIMENTS

Figure 1:
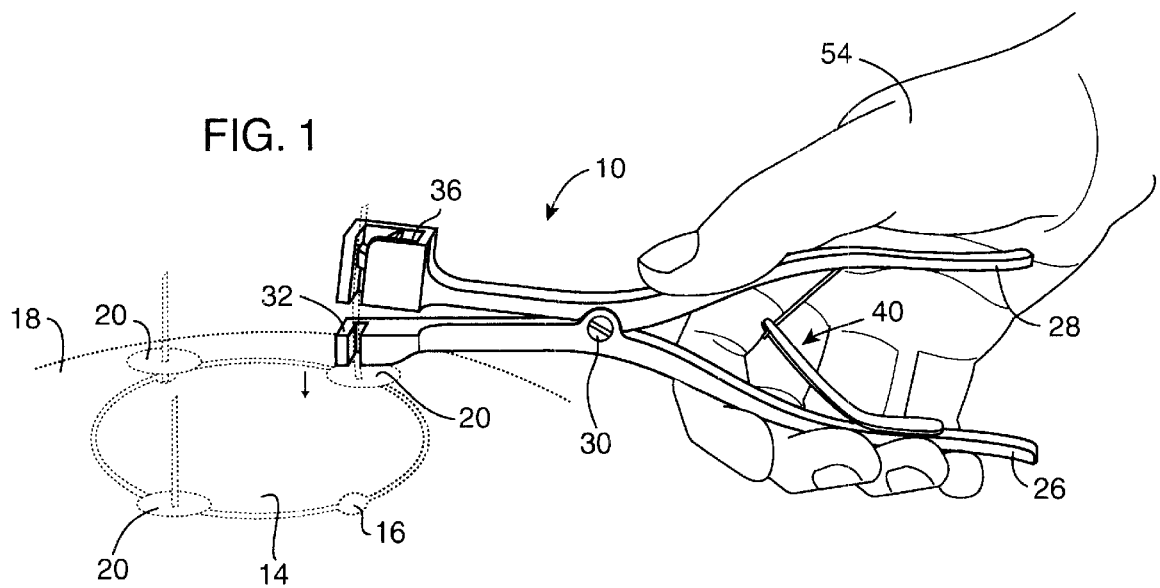
FIG. 1 is a perspective view of a tensioning tool embodying the present invention, illustrating the tensioning of cranial-flap clamps onto a bone flap and cranium, illustrated in phantom.

As shown in the drawings for purposes of illustration, the present invention is concerned with a tensioning tool, generally referred to in the Figures by the reference number 10, and a trimming tool, generally referred to in the Figures by the reference number 12, which are particularly adapted for use in the replacement and fixation of a bone flap 14 after a craniotomy procedure.

With reference to FIG. 1, a craniotomy procedure involves creating a burr hole 16 into the skull or cranium 18 of a patient and subsequently using a high-speed craniotome, or other dissecting or cutting tool to create a typically circular bone flap 14. The bone flap 14 is then removed, or pulled back in order that the surgeon can access the contents of the cranium 18 and perform the necessary procedures. After these procedures are performed, the bone flap 14 is replaced and fixed into position.

The tools 10 and 12 of the present invention are particularly adapted for use with cranial-flap clamps 20 used in locking the cranial bone flap 14 to the cranium 18. Such cranial-flap clamps have opposing closure members 22, such as the illustrated disks, positioned relative to each other on a stem 24, so that as a top closure member 22 is forced downwardly along the length of the stem 24, objects positioned between the two closure members 22 are clamped to one another. Often, such closure members 22 are slightly parabolic and disk shaped, and may even include projections, to enhance the clamping and fixing effect. The stem 24 typically includes ridges or teeth along the length thereof which serve to hold the top closure member 22 in place, while permitting the top closure member 22 to be moved downward given the appropriate force while preventing upward travel of the top closure member. Such stems 24 often include a pressure release mechanism so that a portion of the stem 24 is automatically removed from the clamp 20 once the appropriate tension is achieved. Although such clamps 20 are made of a variety of materials, it is preferable that the clamps 20 be comprised of non-ferromagnetic polymer materials so that the clamps 20 will not interfere with CT or MR imaging. Although the invention is not limited to such, the tools 10 and 12 are particularly adapted for use with the clamps described in U.S. Pat. No. 6,022,351 to Bremer et al., the contents of which are hereby incorporated by reference.

With reference now to FIGS. 3–6, the tensioning tool 10 of the present invention is comprised of a first handle 26 and a second handle 28 attached to one another at pivot point 30 intermediate first and second ends thereof. A first jaw 32 extends from the first end of the first handle 26. The first jaw 32 includes an aperture 34 which is configured to accept the stem 24 therethrough. A second jaw 36 extends from the first end of the second handle 28 and also has an aperture 38 which aligns with the first jaw aperture 34 when the jaws 32 and 36 are brought towards one another, and is configured to accept the stem 24 therethrough. Typically, the first and second jaw apertures 34 and 38 comprise open-faced channels to permit the surgeon to place the tool 10 directly onto the stem 24 of the clamp 20, or approach and insert the stem 24 into the apertures 34 and 38 from the side. While the illustrated configuration provides convenience to the surgeon, it is to be understood that it is merely important that the apertures 34 and 38 align with one another and accept the stem 24 therethrough.

A spring 40, or other appropriate biasing means, is positioned between the first and second handles 26 and 28 for biasing the first and second jaws 32 and 36 into contact with one another. In the particularly preferred illustrated embodiment, the spring 40 comprises a first leaf spring 42 having a first end 44 attached to the second end of the first handle 26, and a second leaf spring 46 having a first end thereof 48 attached to the second end of the second handle 28, with the second ends 50 and 52 of the leaf springs 42 and 46 operably connected to one another. Typically, the second ends 50 and 52 are interlocked with one another by forming an aperture or notch in one end, with the other end having reduced diameter and fitting within the aperture so that flexation can occur without the first and second leaf springs 42 and 46 disconnecting from one another. The first ends 44 and 48 of the leaf springs 42 and 46 can be attached to the second end of the handles 26 and 28 by any appropriate means, including welding, riveting, or the like. The strength of the leaf springs 42 and 46 should be such that the first and second jaws 32 and 36 are biased towards one another, while allowing a surgeon to separate the jaws 32 and 36 by compressing the handles 26 and 28 with his or her hand 54 without excessive effort. As illustrated in FIGS. 5 and 6, the handles 26 and 28 may include raised bumps 56, or other surface irregularities, to enhance the grip of the surgeon.

Referring now to FIGS. 7 and 8, a cavity 58 is formed in the second jaw 36 which houses a ratcheting mechanism, generally referred to by the reference number 60. The cavity 58 is at least partly contiguous with the second jaw aperture 38 so that the ratcheting mechanism 60 can selectively lock the stem 24 in place within the second jaw aperture 38. In the illustrated preferred embodiment, the cavity 58 and second jaw aperture 38 are completely contiguous with one another to form a single cavity. The ratcheting mechanism 60 comprises a pawl attached to the second jaw 36 about pivot point 64, such as by a bolt or similar member extending across the cavity 58 of the second jaw 36. The pawl includes teeth 66 on an outer and upper edge thereof which are configured to press against and lock the stem 24 in place within the second jaw aperture 38 by pressing the stem 24 against a wall 68 of the second jaw 36.

A spring 70 biases the pawl teeth 66 against the second jaw wall 68, resulting in a portion of the pawl 72 to lie without the second jaw 36. The spring 70 is typically wrapped around the pivot point 64, so that an end thereof rests on a lower second jaw wall 74, with the opposite end being attached to the pawl 62 itself.

As illustrated in FIG. 7, when the first jaw 32 is brought into contact with the second jaw 36, the first jaw 32 pushes against the extended portion 72 of the pawl 62 to pivot the pawl 62, resulting in the teeth 66 being removed from the upper second jaw wall 68. In this state, the stem 24 can be inserted through the aligned first and second jaw apertures 34 and 38. However, when the first jaw 32 is moved away from the second jaw 36, by pressing the first and second handles 26 and 28 towards one another, the ratchet spring 70 biases the pawl teeth 66 upward into contact with the second jaw upper wall 68, or stem 24 within the second jaw aperture 38 to hold the stem 24 in place. The pawl teeth 66 can be configured to engage the ratchet teeth or ridges (not shown) of the stem 24 to enhance this locking effect.

Figure 2:
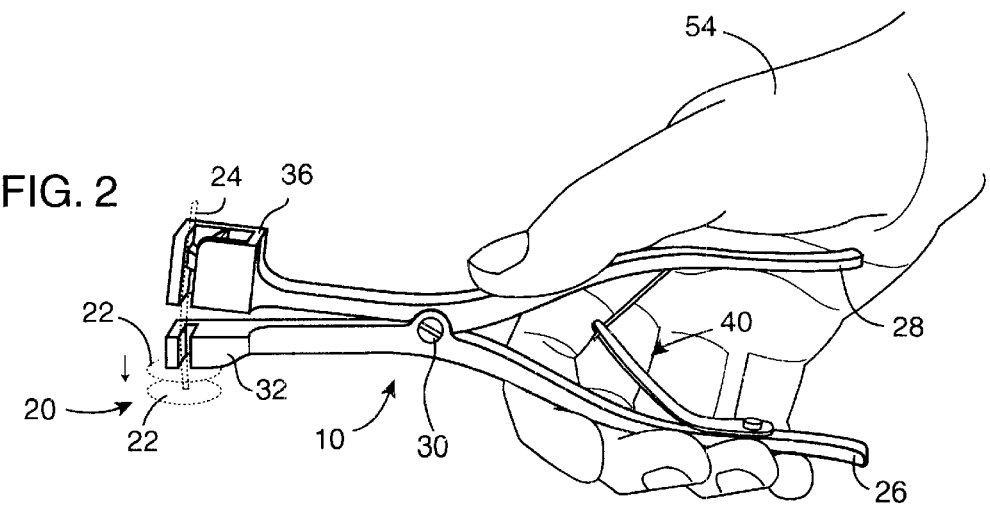
FIG. 2 is a perspective of the tensioning tool of FIG. 1 actuating a cranial-flap clamp in phantom.
Figure 3:
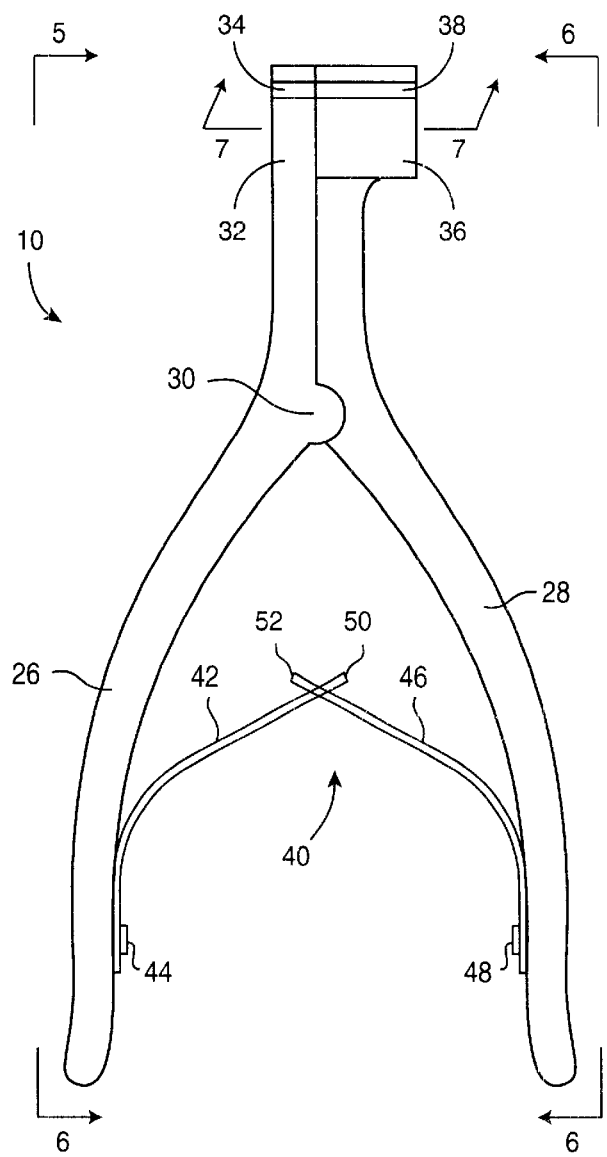
FIG. 3 is a top plan view of the tensioning tool of the present invention.
Figure 4:
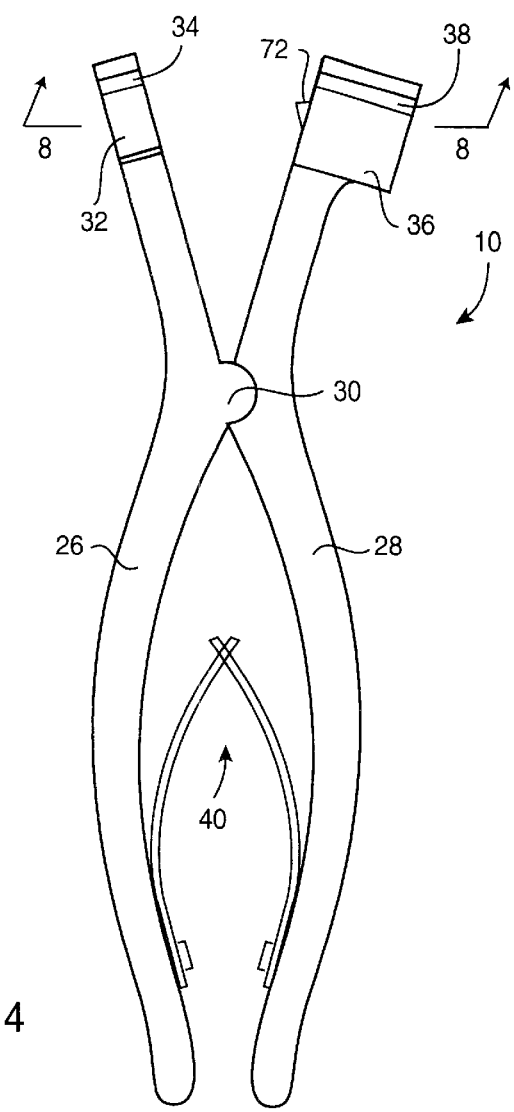
FIG. 4 is a top plan view of the tensioning tool of FIG. 3 in an opened state.

With reference again to FIGS. 1 and 2, after the craniotomy is performed, the cranial bone flap 14 is repositioned, and the clamps 20 inserted between the cranium 18 and bone flap 14 so that the lower closure member 22 rests beneath the cranium 18, while the upper closure member 22 is spaced above the cranium 18 and bone flap 14. Preferably, these clamps 20 are spaced equidistant from one another so that an equal amount of force is applied to the outer circumference of the bone flap 14. Sutures, such as tack-up sutures (now shown), may be applied between the clamps 20 for added support. With the clamp 20 in place, the stem 24 is inserted into the first and second jaw apertures 34 and 38. The tool 10 is positioned such that the first jaw 32 rests upon the top closure member 22. The handles 26 and 28 are then compressed by the surgeon's hand 54, resulting in the first and second jaws 32 and 36 being removed from one another, the pawl 62 pivoting such that the teeth 66 thereof lock the stem 24 in place within the second jaw aperture 38, while the first jaw 32 moves the upper closure member 22 downward. Preferably, the clamps 20 are all tensioned so that the upper closure member 22 contacts the cranium 18 and bone flap 14. At this point, tensioning is continued on each clamp 20 until a predetermined amount of tension is achieved, or the safety tab portion of the stem 24 automatically breaks off indicating that the appropriate tension has been achieved.

Figure 9:
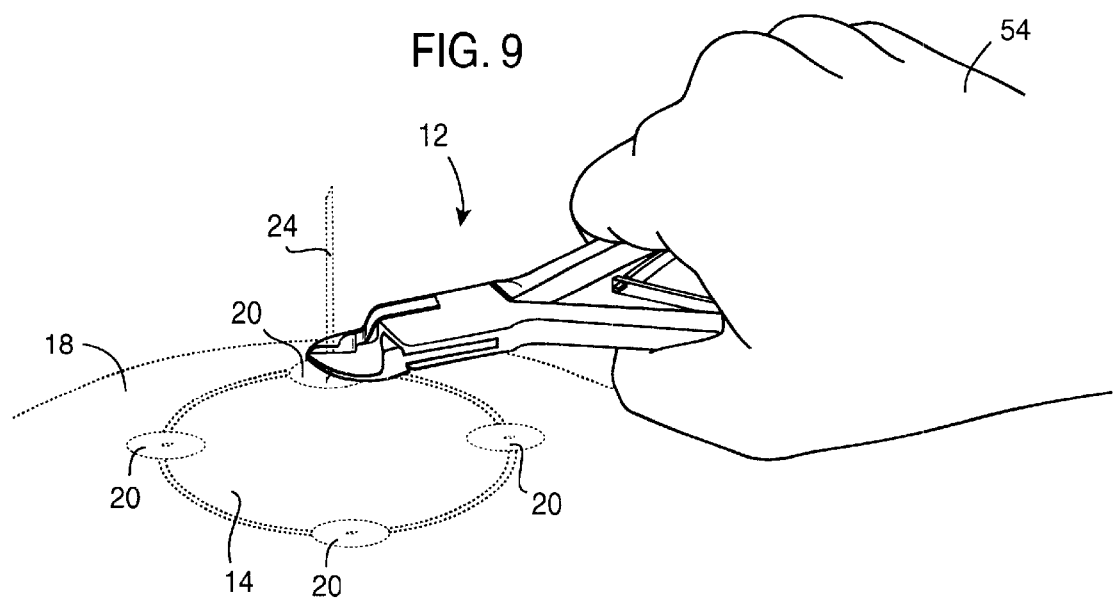
FIG. 9 is a perspective view of a trimming tool embodying the present invention removing a stem from a cranial-flap clamp tensioned onto a bone flap and cranium.
Figure 10:
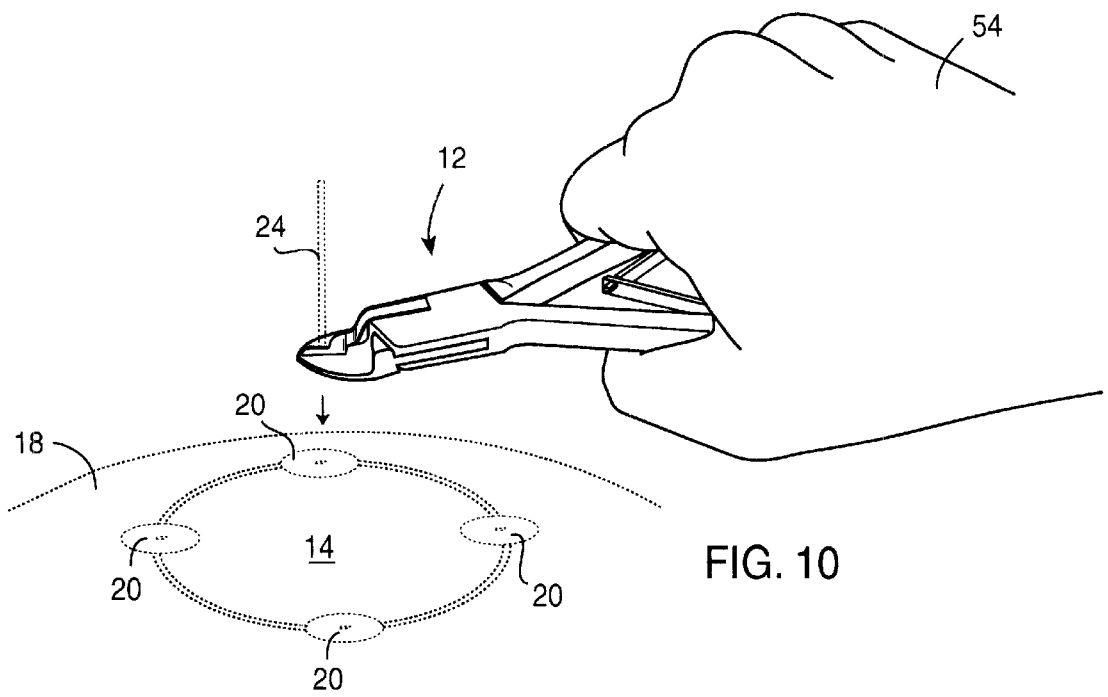
FIG. 10 is a perspective view of the trimming tool of FIG. 9, illustrating the retention of the cut stem within jaws of the trimming tool.

With reference to FIGS. 9 and 10, after the clamp 20 has been properly tensioned onto the bone flap 14 and cranium 18, the stem 24, or the remainder thereof, is removed. Although this can be accomplished using a variety of trimming and cutting tools, the present invention provides a particularly useful trimming tool 12 which retains the cut portion of the stem 24 within the tool 12, as illustrated in FIG. 10, so that it is not accidentally left within the open wound area.

With reference now to FIGS. 11–14, the trimming tool 12 generally comprises first and second handles 76 and 78 pivotally attached to one another intermediate the first and second ends thereof. A first cutting jaw 80 extends from the first end of the first handle, and a second cutting jaw 82 extends from the first end of the second handle. The first and second cutting jaws 80 and 82 are configured to cooperatively cut an object, such as the stem 24 when closed towards one another. Such a handle and cutting jaw arrangement is well known in the art.

Figure 11:
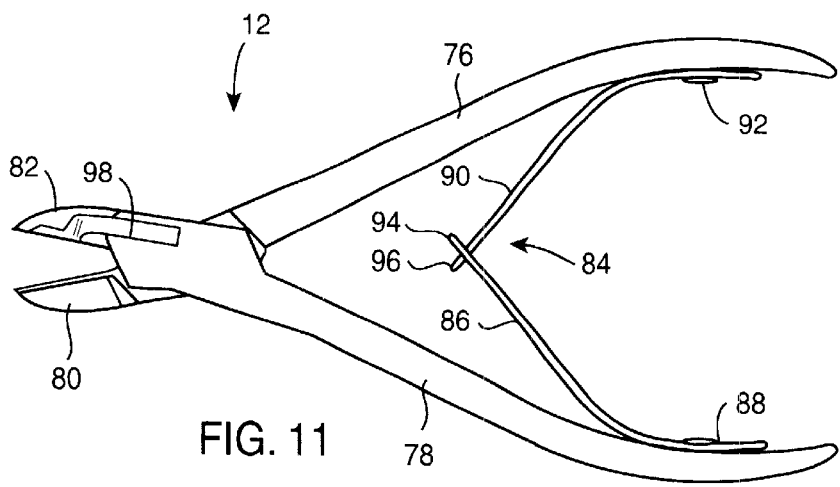
FIG. 11 is a top planar view of the trimming tool of the present invention in an opened state.
Figure 12:
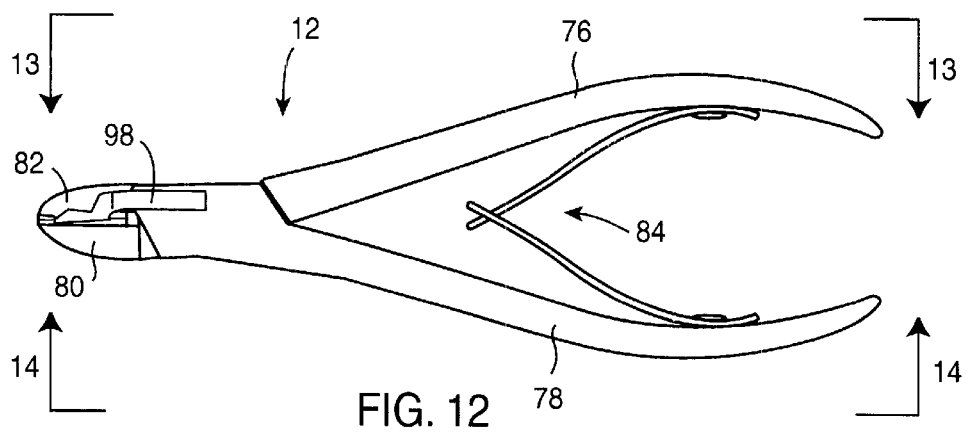
FIG. 12 is a top plan view of the trimming tool of the present invention in a closed state.

A spring, generally referring to by the reference number 84 is interposed between the first and second handles 76 and 78 for biasing the first and second jaws 80 and 82 into an open position, as illustrated in FIG. 11. In the illustrated preferred embodiment, the spring 84 comprises a first leaf spring 86 having a first end 88 attached to the second end of the first handle 76, and a second leaf spring 90 having a first end thereof 92 attached to the second end of the second handle 78, with the second ends 94 and 96 of the leaf springs 86 and 90 operably connected to one another. Typically, the second ends 94 and 96 are interlocked with one another by forming an aperture or notch in one end, and with the other end being of reduced diameter and fitting within the aperture so that flexation can occur, without the first and second leaf springs 86 and 90 disconnecting from one another. The first ends 88 and 92 of the leaf springs 86 and 90 can be attached to the second end of the handles 76 and 78 by any appropriate means, including welding, riveting, or the like. The strength of the leaf springs 86 and 90 should be such that the first and second jaws 80 and 82 are biased towards one another, while allowing a surgeon to separate the jaws 80 and 82 by compressing the handles 76 and 78 with his or her hand 54 without excessive effort.

Figure 13:
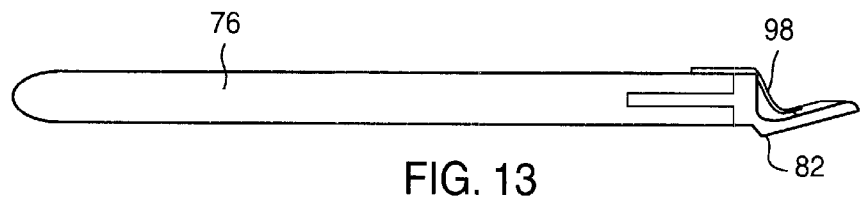
FIG. 13 is a side elevational view taken generally along line 13—13 of FIG. 12.
Figure 14:
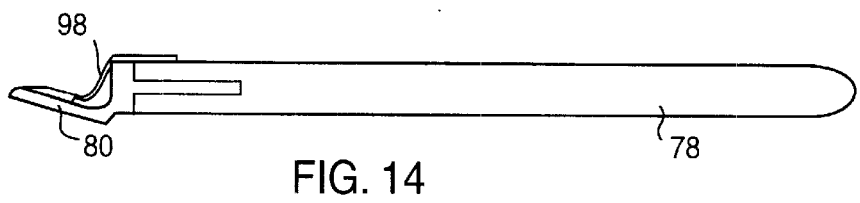
FIG. 14 is a side elevational view taken generally along line 14—14 of FIG. 12.

A clip 98 is associated with either the first or second cutting jaw 80 or 82 and is configured to retain the cut object, such as the illustrated stem 24, between the clip 98 and the closed jaws 80 and 82 until the jaws 80 and 82 and are separated from one another, or the object is forcible removed from the clip 98. The clip 98 is typically generally S-shaped, with a first end 100 attached to the associated first or second jaw 80 or 82. The first end 100 of the clip 98 can actually be fitted into a recess formed in the first or second jaw 80 and 82 or 82. The remainder of the clip 98 extends over the jaw 80 or 82 in stepped fashion so that the second end 102 of the clip 98 rests above a cutting edge 104 of the jaw 80 or 82, as illustrated in FIGS. 13 and 14.

With reference now to FIGS. 15–18, the second clip end 102 is actually bent so that it lies transverse to the longitudinal axis of the remainder of the clip 98 and is positioned directly over the cutting edge 104 of the jaw 80 or 82. Preferably, the second end 102 includes a sharpened edge 106, as will be described more fully herein.

The stem 24 is placed between the open jaws 80 and 82, as illustrated in FIG. 15. The handles 76 and 78 are then compressed causing the jaws 80 and 82 to come into contact with one another and cut the stem 24, as illustrated in FIG. 16. With particular reference to FIGS. 17 and 18, the clip 98 is in a downward and resting position when the jaws 80 and 82 are separated from one another. However, upon closing the jaws 80 and 82 together, the cutting edges 104 of the jaws 80 and 82 serve to cut the stem 24, while the second end 102 of the clip 98 is flexed upward by contact with the stem 24. With the jaws 80 and 82 in closed position, the stem 24 is compressibly retained between the clip 98 and jaws 80 and 82. Thus, the surgeon can keep the jaws 80 and 82 in closed position with the stem 24 retained therein to safely remove the stem 24 for disposal. The sharpened edge 106 of the clip 98 facilitates this retention by cutting into a portion of the stem 24 to more securely hold the stem 24 in place.

The sharpened edge 106 may in some instances actually retain the stem 24 even when the jaws 80 and 82 are opened from one another. In this case, the stem 24 is removed by grasping the stem 24 and pulling it away from the clip 98.

The trimming tool 12 is designed such that the stem 24 is removed nearly flush with the top closure member 22. This prevents unsightly bumps, or undue irritation, when the scalp is placed over the cranium 18 after the procedure.

Although the trimming tool 12 has been illustrated and described with respect to a craniotomy procedure, it is to be understood that the retention aspect of this tool 12 could conceivably be taken advantage of in other applications.

The tools 10 and 12 of the present invention are advantageous to prior existing tools in that they are intuitive and easy to use with a single hand. This frees the other hand of the surgeon to do other things, such as holding or positioning the clamp 20. The tools 10 and 12 are fairly simple in construction, making them inexpensive in comparison to other devices. No calibration nor assembly is required before their use. The tools 10 and 12 are capable of being reused and sterilized with conventional methods, such as autoclave, without disassembly. Although the tools 10 and 12 are preferably comprised of a durable and sterilizable material, such as steel, they can also be disposable and comprised of plastic or the like.

Although several embodiments have been described in detail for purposes of illustration, various modifications of each may be made without departing from the scope and spirit of the invention. Accordingly, the invention is not to be limited, except as by the appended claims.

What is claimed is:

1. A crainial flap fastening system, comprising:
    a cranial-flap clamp comprising a first closure member at an end thereof, a stem extending upwardly from the first closure member, and a second closure member slidably connected to the stem; and
    a cranial-flap clamp tensioning tool comprising:
        first and second handles pivotally attached to one another intermediate ends thereof;
        spring means for biasing the first and second jaws into contact with one another;
        a first jaw extending from the first end of the first handle and having an aperture configured to accept the stem therethrough;
        a second jaw extending from the first end of the second handle and having an aperture configured to align with the aperture of the first jaw and accept the stem therethrough; and
        a ratcheting mechanism associated with the second jaw for selectively locking the stem in place within the second jaw aperture;
        whereby the first and second closure members are fastened relative to one another upon positioning the first jaw over the second closure member and inserting the stem through the apertures of the first and second jaws and moving the jaws away from one another, causing the stem to be gripped by the ratcheting mechanism and the second closure member to be slid towards the first closure member.

2. The system of claim 1, wherein the spring means comprises first and second leaf springs, a first end of the first leaf spring being attached to the second end of the first handle, a first end of the second leaf spring being attached to the second end of the second handle, wherein the second ends of the first and second leaf springs are connected to each other.

3. The system of claim 1, wherein the ratcheting mechanism comprises a pawl pivotally attached to the jaw and having teeth on an outer edge thereof, and a spring associated with the jaw and the pawl to bias the pawl in a locking position.

4. The system of claim 3, wherein the ratcheting mechanism is positioned within a cavity of the second jaw which is at least partially contiguous with the aperture of the second jaw.

5. The system of claim 4, wherein a portion of the pawl extends without the second jaw when the pawl is in its biased position.

6. The system of claim 3, wherein the first jaw is configured to contact the pawl and position the pawl in an unlocked position when the first and second jaws are brought towards one another.

7. The system of claim 1, wherein the first jaw aperture comprises an open-faced channel extending the width of the first jaw.

8. The system of claim 1, wherein the second jaw aperture comprises an open-faced channel extending the width of the second jaw.

9. The system of claim 1, wherein the stem of the cranial-flap clamp is adapted to break upon a predetermined tension between the first and second closure members.

10. The system of claim 1, including a trimming tool for trimming the stem above the tensioned first and second closure members.

* * * * *